United States Patent [19]
Glaug et al.

[11] Patent Number: 5,601,545
[45] Date of Patent: Feb. 11, 1997

[54] DISPOSABLE ABSORBENT ARTICLE WITH IMPROVED WAIST CONTAINMENT AND GASKETING

[75] Inventors: Frank S. Glaug, Appleton; Robert L. Popp, Hortonville; Richard H. Thiessen, Appleton, all of Wis.

[73] Assignee: Kimberly-Clark Corporation, Neenah, Wis.

[21] Appl. No.: 268,054

[22] Filed: Jun. 29, 1994

[51] Int. Cl.⁶ ........................................ A61F 13/15
[52] U.S. Cl. ........................... 604/385.2; 604/393
[58] Field of Search ........................... 604/373, 378, 604/385.1, 385.2

[56] References Cited

U.S. PATENT DOCUMENTS

| | | | |
|---|---|---|---|
| 5,171,239 | 12/1992 | Igaue et al. | 604/385.2 |
| 5,236,428 | 8/1993 | Zajaczkowski | 604/385.2 |
| 5,360,420 | 11/1994 | Cook et al. | 604/378 |
| 5,366,453 | 11/1994 | Zehner et al. | 604/378 |

FOREIGN PATENT DOCUMENTS

| | | | |
|---|---|---|---|
| 0196654 | 10/1986 | European Pat. Off. | A61F 13/18 |
| 0252413 | 1/1988 | European Pat. Off. | A41B 13/02 |
| 0272683 | 6/1988 | European Pat. Off. | |
| 0352207 | 1/1990 | European Pat. Off. | |
| 0426227 | 5/1991 | European Pat. Off. | A61F 13/15 |
| 0443082 | 8/1991 | European Pat. Off. | |
| 0455607 | 11/1991 | European Pat. Off. | A61F 13/15 |
| 0543116 | 5/1993 | European Pat. Off. | |
| 0539703 | 5/1993 | European Pat. Off. | A61F 13/15 |
| 2266464 | 11/1993 | United Kingdom . | |
| 2293108 | 3/1996 | United Kingdom . | |
| 9110416 | 7/1991 | WIPO | A61F 13/15 |
| 9111165 | 8/1991 | WIPO . | |
| 9309745 | 5/1993 | WIPO . | |
| 96/01609 | 1/1996 | WIPO . | |
| 96/01608 | 1/1996 | WIPO . | |
| 96/01607 | 1/1996 | WIPO . | |

*Primary Examiner*—Robert A. H. Clarke
*Attorney, Agent, or Firm*—Douglas L. Miller

[57] ABSTRACT

A disposable absorbent article having improved containment at the waist portion thereof comprises an absorbent layer and a surge layer in liquid communication therewith, and a liquid impermeable baffle layer overlying portions of the absorbent layer and the surge layer. The front edge of the absorbent structure is spaced from the back edge of a waist elastic member by a selected separation distance, thereby enhancing the gasketing effect of the waist elastic member on the article.

11 Claims, 9 Drawing Sheets

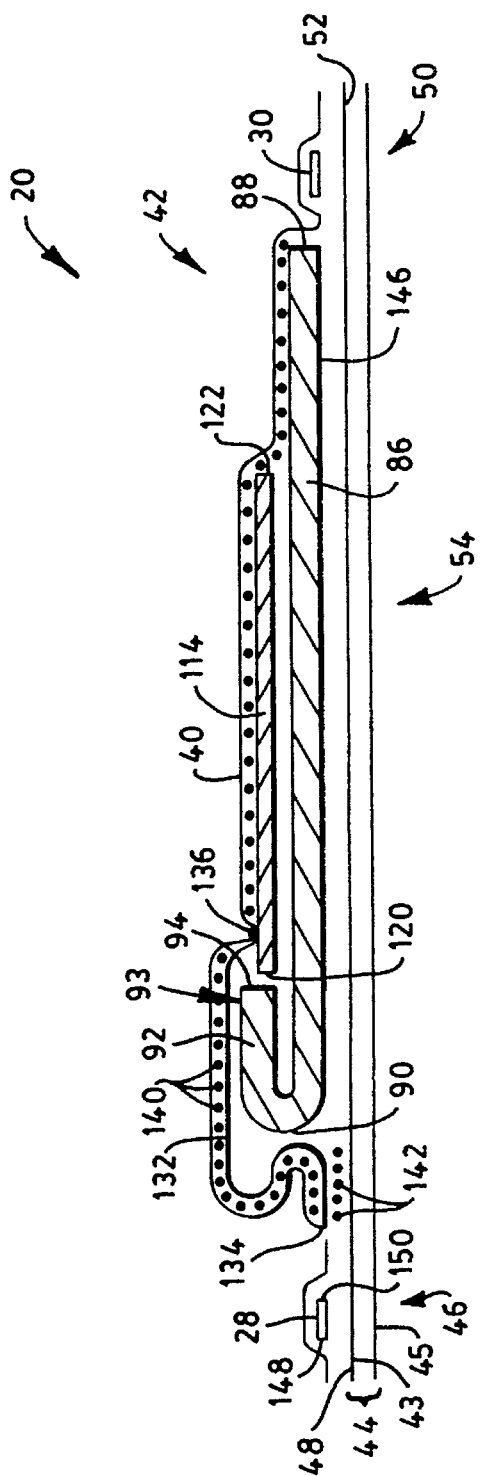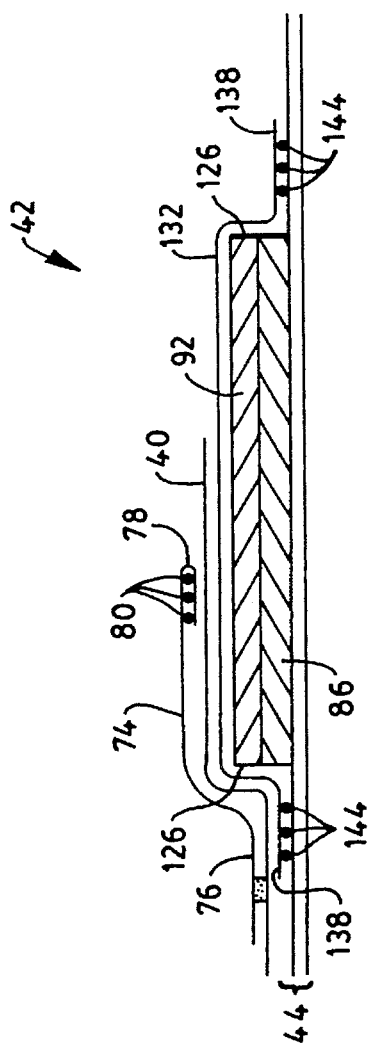

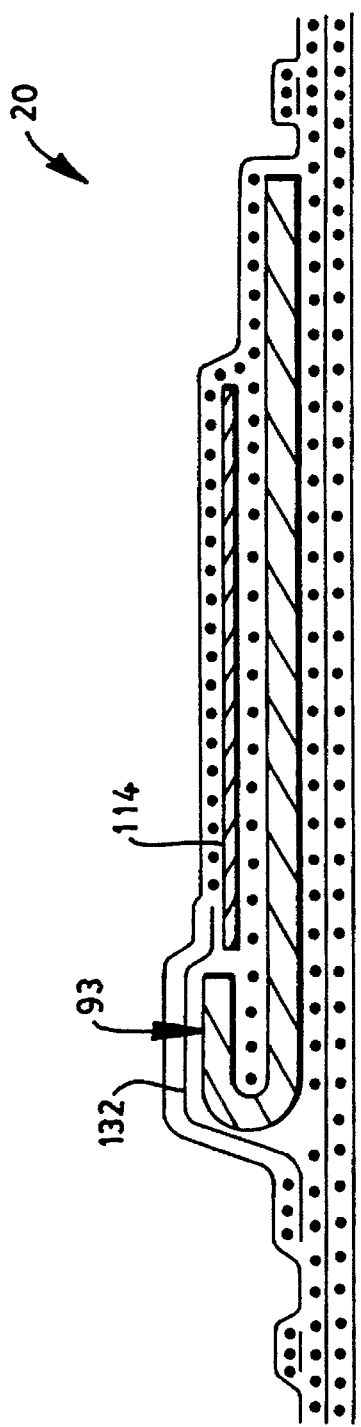
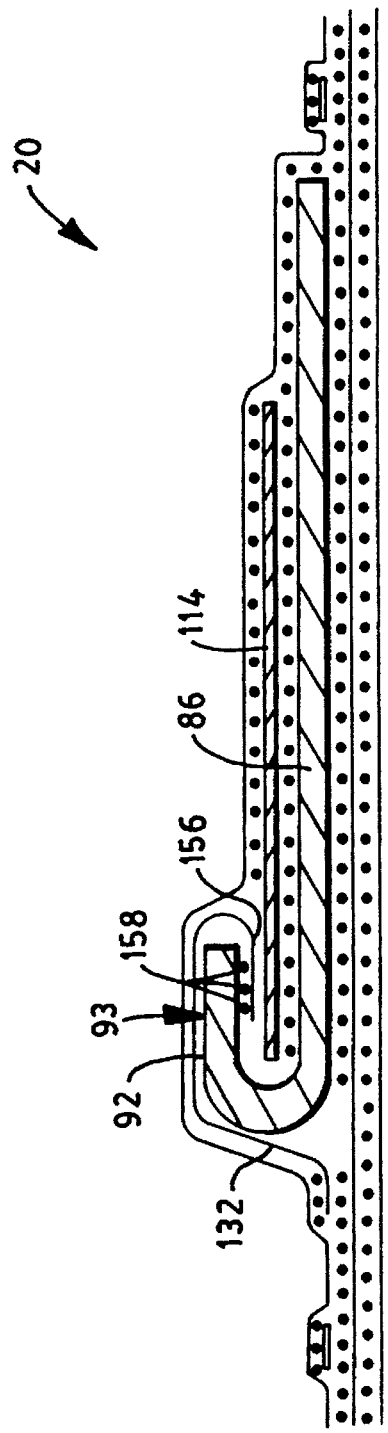

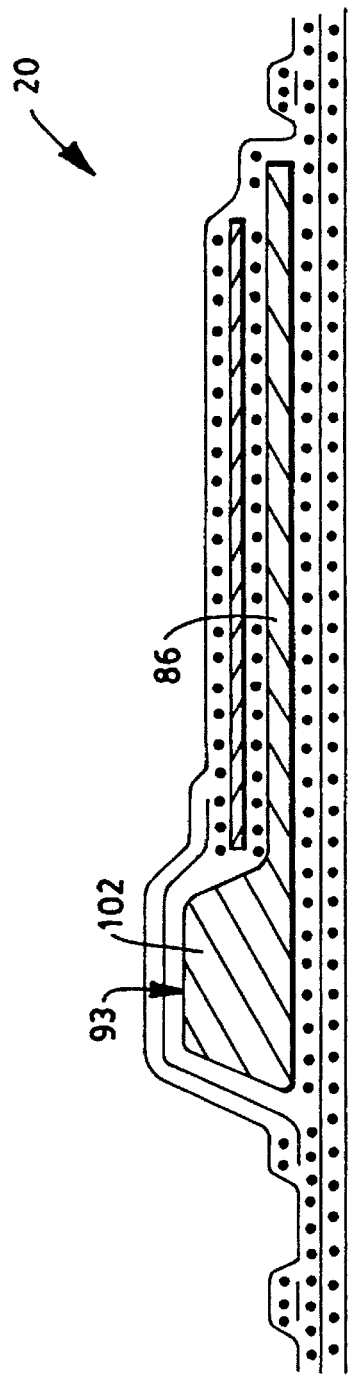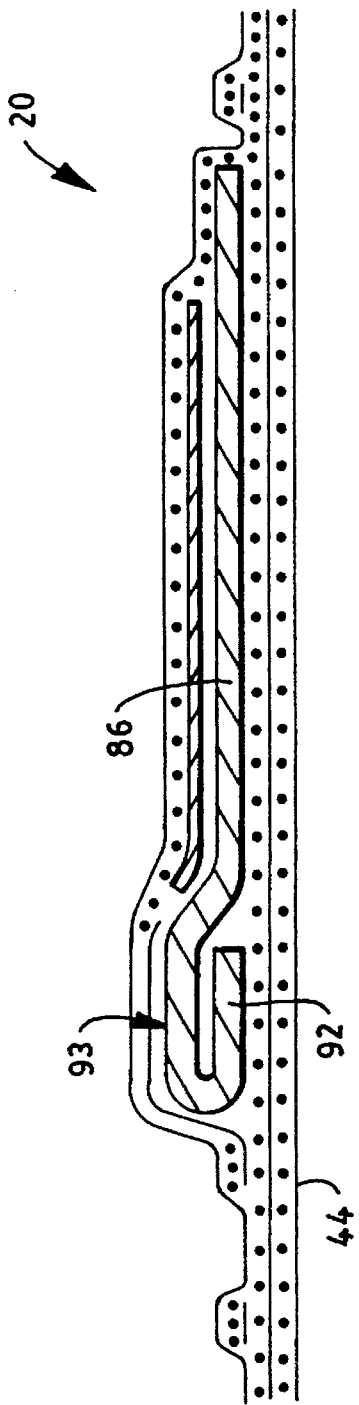

5,601,545

DISPOSABLE ABSORBENT ARTICLE WITH IMPROVED WAIST CONTAINMENT AND GASKETING

BACKGROUND OF THE INVENTION

The present invention relates to disposable absorbent articles, and more particularly to a disposable absorbent article having improved containment and gasketing at the waist.

Disposable absorbent articles have been designed and constructed for various purposes. For example, some have been designed for use as diapers for babies, some as training pants for younger children in the potty-training stage, and some as incontinence products for adults. One of the most important features of any disposable absorbent article is that it should contain liquid and other waste material within the article itself. Failure to do so results in leakage and consequent wetting of clothes.

Generally, leakage will occur at the leg openings and the waist opening. In order to prevent leakage at these openings, stretched elastic members have been attached at the leg and waist openings in order to provide an elastic gasketing effect about the legs and waist of the wearer. Current absorbent articles include various designs incorporating these elastic members with the intent of containing liquid and waste matter. They have not, to date, been entirely successful in this area.

For example, if the wearer of a disposable absorbent article urinates at a flow rate or in a quantity that exceeds the absorption rate or absorption capacity of the article, the urine most often will pool at the leg and waist openings. Pooling at the leg and waist openings very often results in urine leakage. This leakage will occur more often at the leg openings than at the waist opening, especially during the daytime. However, when the wearer is in the prostrate position, such as when the wearer is lying down asleep, leakage is just as likely to occur at the waist as at the legs.

Thus, there still exists a need for improving waste containment at the wearer's waist.

SUMMARY OF THE INVENTION

The present invention provides a disposable absorbent article having improved waste containment and gasketing at the waist portion thereof. This improvement includes improving the absorption capacity at the waist portion of the article, and enhancing the gasketing effect at the waist portion by providing a selected separation distance between a waist elastic member and the edge of the absorbent layer.

In one form of the present invention there is provided a disposable absorbent article comprising a backsheet including a front portion with a front edge and a back portion with a back edge, and an absorbent structure on the backsheet. The absorbent structure includes an absorbent layer including a front edge and a back edge, and a surge layer on the absorbent layer. The surge layer includes a front edge and a back edge that are respectively spaced inwardly of the absorbent layer front edge and back edge. A liquid impermeable baffle layer overlies a portion of the absorbent layer.

In another form of the present invention there is provided a disposable absorbent article comprising a backsheet and an absorbent structure on the backsheet. The absorbent structure includes an absorbent layer including a front portion, a crotch portion, and a rear portion; an absorbent panel on the front portion of the absorbent layer; and a surge layer at least on the crotch portion of the absorbent layer. A liquid impermeable baffle layer overlies both the absorbent panel and a portion of the surge layer.

In still another form of the present invention there is provided a disposable absorbent article including a backsheet including a front portion with a front edge, and a back portion with a back edge, and an absorbent structure on the backsheet. The absorbent structure includes a front section having a front section thickness and a front section surface, and a back section having a back section thickness and a back section surface. The front section thickness is greater than the back section thickness, and so defines an inner absorbent wall extending between the front section surface and the back section surface. A surge layer is positioned on the back section of the absorbent layer and is in substantial liquid communication with the inner absorbent wall.

In still yet another form of the present invention there is provided a disposable absorbent article including a backsheet, and an absorbent structure on the backsheet. The absorbent structure includes an absorbent layer including a front portion, a crotch portion, and a rear portion; an absorbent panel on the front portion of the absorbent layer; and a surge layer at least on the crotch portion and having a portion thereof between the absorbent layer and the absorbent panel. A liquid impermeable baffle layer overlies the absorbent panel.

In still yet a further form of the present invention there is provided a disposable absorbent article comprising a backsheet and an absorbent layer on the backsheet, in which the absorbent layer has a front portion, a crotch portion, and a rear portion. The front portion of the absorbent layer has an absorbent capacity greater than either the crotch portion or the rear portion. A liquid impermeable baffle layer overlies at least a portion of the front portion of the absorbent layer.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein:

FIG. 3 illustrates a cross-sectional view of FIG. 2 taken along line 3—3 and viewed in the direction of the arrows;

FIG. 4 illustrates a cross-sectional view of FIG. 2 taken along line 4—4 and viewed in the direction of the arrows;

FIG. 7 illustrates a modification of the view of FIG. 3;

FIG. 8 illustrates a modification of the view of FIG. 3;

FIG. 9 illustrates a modification of the view of FIG. 3;

FIG. 10 illustrates a modification of the view of FIG. 3;

DETAILED DESCRIPTION

Figure 1:
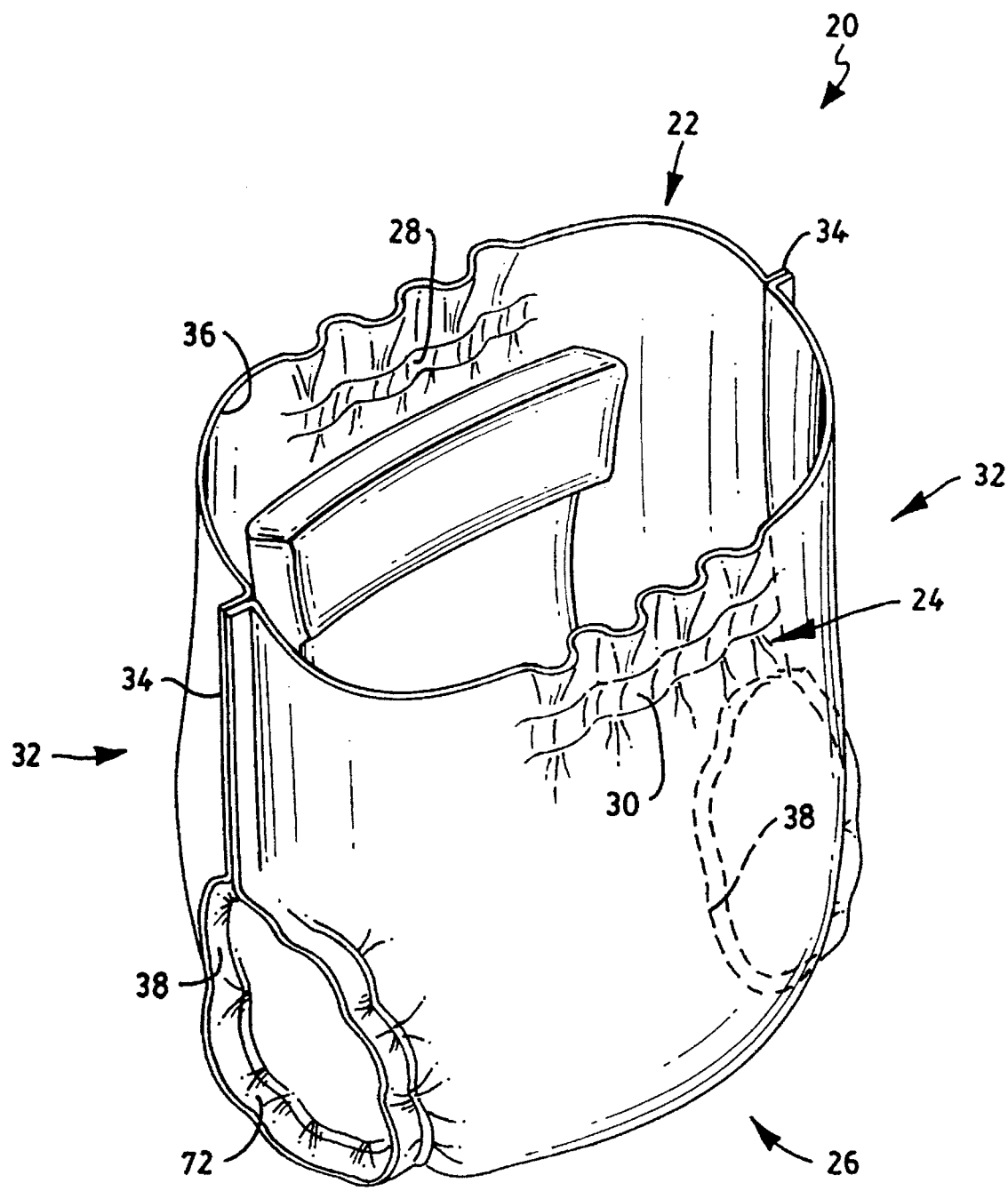
FIG. 1 is a perspective view illustrating one type of a disposable absorbent article incorporating the principles of the present invention.

Referring primarily to FIG. 1, there is illustrated a disposable absorbent article 20 in the form of a child's training pant comprising a front waist portion 22, a back waist portion 24, and an article crotch portion 26. Front waist portion 22 includes front waist elastic member 28 and back waist portion 24 includes rear waist elastic member 30. Article 20 further comprises a pair of side portions 32, each of which includes a seam 34 extending between a waist opening 36 and a respective leg opening 38.

Although article 20 is illustrated and described as a training pant, the present invention can be utilized in other types of absorbent articles, such as baby diapers, adult incontinence products, or the like. The term "disposable" means that article 20 is designed to be used until soiled, either by urination or otherwise, and then discarded, rather than being washed and used again.

Figure 2:
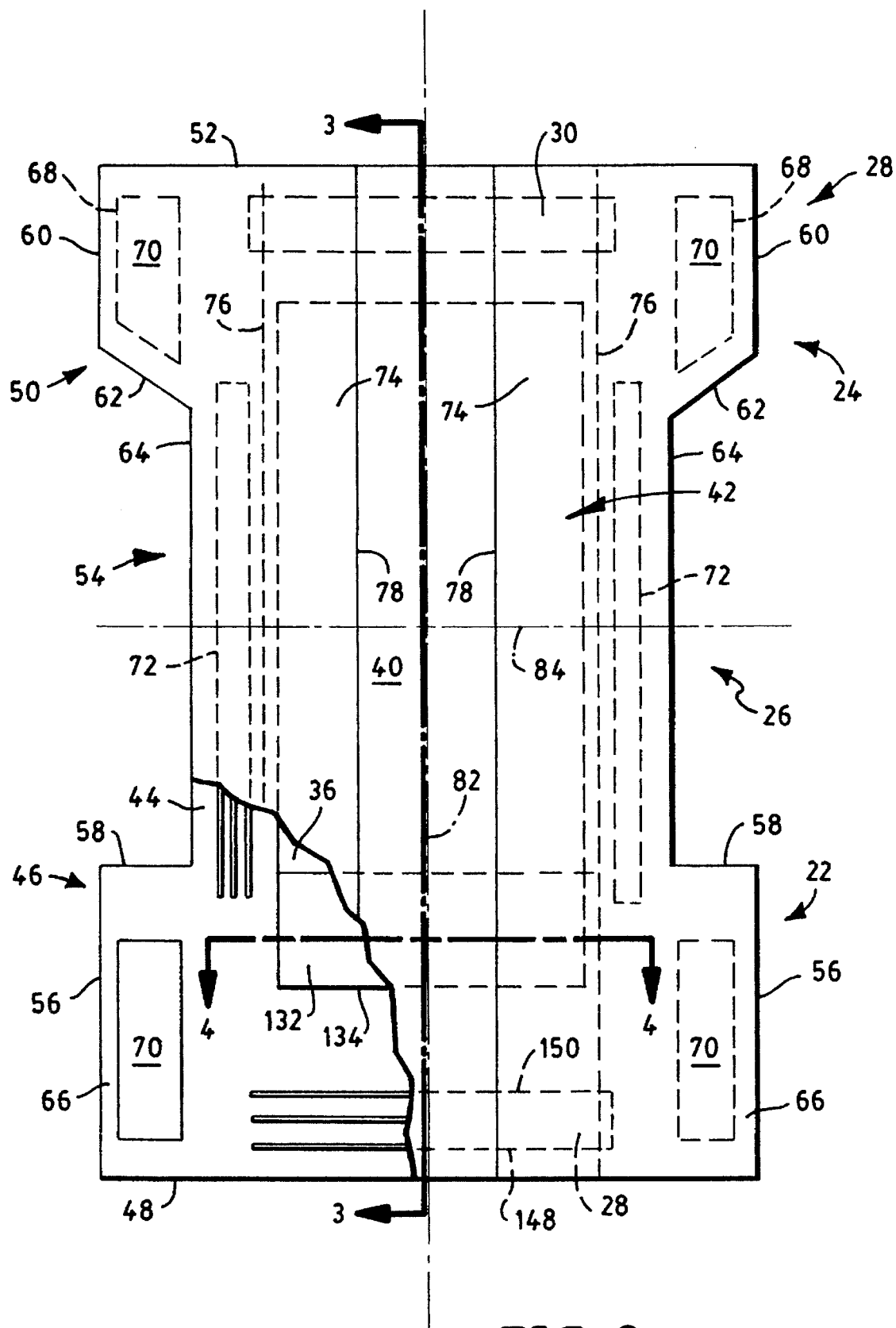
FIG. 2 illustrates a top plan, partially broken-away view of the absorbent article in FIG. 1 in a partially disassembled, stretched flat state.

With reference to FIG. 2, article 20 comprises a liner or topsheet 40, an absorbent structure 42, and an outer cover or backsheet 44. Topsheet 40 faces toward the body of the user, and may or may not be the layer that directly contacts the skin of the wearer. Backsheet 44 is on the side of absorbent structure 42 opposite from topsheet 40, and may or may not be the outermost layer of disposable absorbent article 20.

As illustrated in FIGS. 2 and 3, topsheet 40 is superimposed over backsheet 44 so as to be coincident therewith. However, topsheet 40 or backsheet 44 can have any dimension suitable for other designs or constructions. Backsheet 44 comprises front portion 46 with front edge 48, back portion 50 with back edge 52, and crotch portion 54. Backsheet 44 further comprises front outer edges 56 (FIG. 2), front transverse edges 58, back outer edges 60, back sloping edges 62, and inner edges 64 respectively extending between front transverse edges 58 and back sloping edges 62. These edges of backsheet 44 define front side sections 66 and back side sections 68. When article 20 is folded to align a respective front outer edge 56 and a back outer edge 60, these aligned edges can be bonded to form a seam 34, thereby forming waist opening 36 and leg openings 38. The front outer edges 56 and back outer edges 60 can be bonded in any suitable manner, such as by ultrasonic bonding, thermal bonding, adhesive bonding, stitching, or the like.

Still referring to FIG. 2, each side section 66, 68 has an elastic area or panel 70 joined thereto in order to provide elasticity to a respective side section 66, 68, and thus to side portions 32 (FIG. 1). The two elastic areas 70 disposed on front side sections 66 can have the same or different geometry or elasticity from the two elastic areas 70 on back side sections 68. The geometry and elastic characteristics of each elastic area 70 can be designed or configured in any desired manner appropriate to the size, shape, and end use of a disposable absorbent article 20. Elastic areas 70 can be incorporated with side sections 66, 68 in any suitable manner, and examples of such incorporation are disclosed in U.S. patent application Ser. No. 08/043,132 filed Mar. 25, 1993, the content of which is incorporated by reference herein. Another example is disclosed in U.S. Pat. No. 4,940,464, inventor Van Gompel et al., the content of which is incorporated by reference herein. Elastic areas 70 can be formed with multiple strands of elastic material arranged in any orientation, such as parallel, intersecting, diagonal, or any combination thereof, or can be a film or laminate of various types of elastomeric material.

Backsheet 44 can be liquid permeable or liquid impermeable, and may or may not have breathability, i.e., be vapor permeable. A suitable liquid permeable backsheet 44 is a nonwoven bicomponent web having a basis weight of about 27 grams per square meter (gsm). The nonwoven bicomponent web may be a spunbond bicomponent web, or a bonded carded bicomponent web. The nonwoven bicomponent web also may comprise spunbond bicomponent filaments, or may be a bonded carded web comprising bicomponent staple fibers. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end or the like. Backsheet 44 also can be a liquid permeable spunbond polypropylene nonwoven web having a basis weight of about 27 gsm.

A suitable liquid impermeable backsheet 44 is a 0.015 mm polyethylene film available from Edison Plastics Company, South Plainfield, N.J. As illustrated in FIG. 3, backsheet 44 can also be a two-ply laminate, in which the innermost layer 43 can be the above-described liquid impermeable film or any other suitable liquid impermeable layer, and the outermost layer 45 can be the above-described liquid permeable spunbond polypropylene nonwoven web or any other suitable liquid permeable layer.

Liquid permeable topsheet 40 can be made of the same material as liquid permeable backsheet 44, or can be made of the same material as liquid impermeable backsheet 44 with apertures therethrough so as to make the material liquid permeable.

These layers can be joined together in any suitable manner. For example, layers 43, 45, as well as the other layers and structure described herein, can be joined together by adhesive bonding. Suitable adhesives can be obtained from Findley Adhesives, Inc., Wauwatosa, Wis. The adhesives can be applied in any manner such as by spraying, slot-coat extrusion, printing, or the like. The applied adhesive can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

Use of the term "join", "joined", "joining", or variations thereof in describing the relationship between two elements means that the two elements can be connected together by heat sealing, ultrasonic bonding, adhesive bonding, stitching, or the like. Further, the two elements can be joined directly together, or may have one or more elements interposed between them, all of which are suitably connected together.

Referring to FIGS. 2 and 4, article 20 further comprises leg elastics 72 (FIG. 2) joined in a stretched condition desirably to both backsheet 44 and topsheet 40. A pair of containment flaps 74 extend between front edge 48 and back edge 52, and have their respective proximal edges 76 joined to topsheet 40. Distal edges 78 of containment flaps 74 include respective flap elastic members 80. Various materials of which flap elastic members 80, leg elastics 72, and waist elastic members 28, 30 can be made are described in the aforementioned and incorporated U.S. Pat. No. 4,940,464 and U.S. patent application Ser. No. 08/043,132; as well as U.S. Pat. No. 4,704,116, inventor Enloe, which is incorporated by reference herein.

One suitable elastic construction for containment flaps 74 is a plurality of strands of LYCRA® 940 decitex that are joined at their ends to backsheet 44 while at an elongation of about 300 percent. Each individual strand is desirably spaced from an adjacent strand by about 3 millimeters. These elastic strands can be obtained from E. I. Du Pont de Nemours Company, Wilmington, Del. Other suitable elastic materials include natural rubber, synthetic rubber, or thermoplastic elastomeric polymers. These elastic materials may also be heat-elasticizable, and can be single or multiple ribbons of elastic material. Generally, leg elastics 72 and flap elastic members 80 are joined to their respective layer or layers while in a stretched condition. Preferably, waist elastic members 28, 30 are a heat-elasticizable material that are joined in their latent state to their respective layer or layers, and thereafter appropriately treated, such as by heat radiation, to recover their elasticity.

Referring now to FIG. 3, absorbent structure 42 comprises absorbent layer 86, absorbent panel 92, and surge layer 114. Absorbent layer 86 comprises back edge 88, front edge 90, and absorbent panel 92 is, in FIG. 3, formed by folding absorbent layer 86 upon itself. Absorbent panel 92 and absorbent layer 86 form a front absorbent area 93 having a bulk thickness, in this specific embodiment, greater than that of absorbent layer 86. Front absorbent area 93 includes an inner absorbent wall 94.

Figure 12:
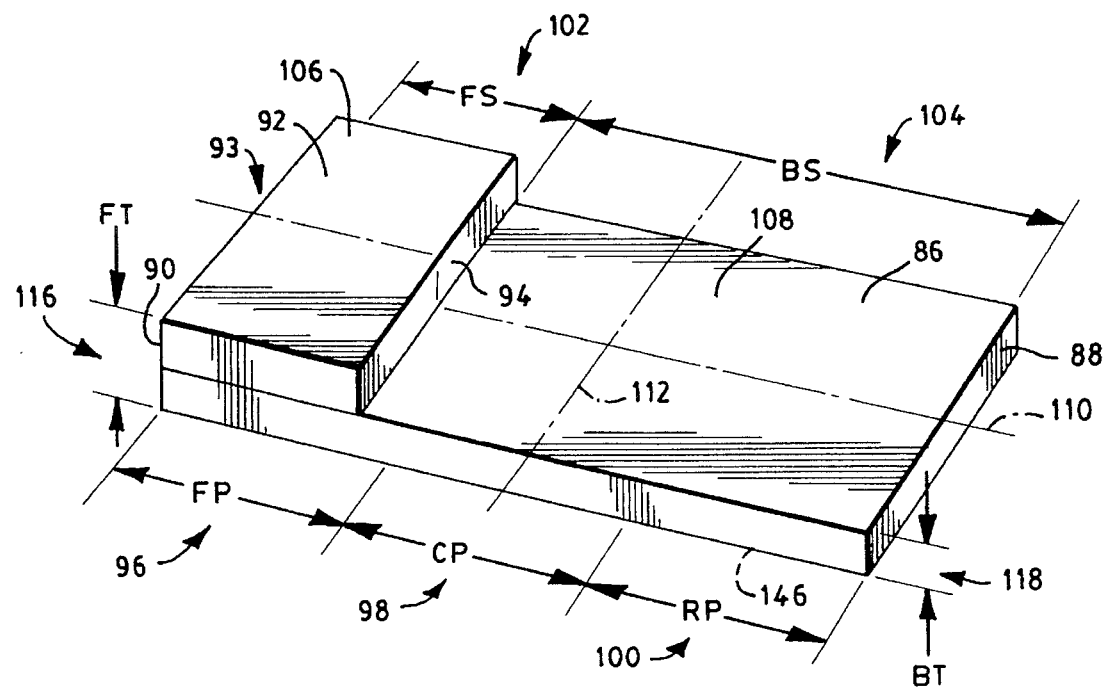
FIG. 12 illustrates a top perspective view of one absorbent.

Referring now primarily to FIG. 12, absorbent layer 86 further comprises front portion 96, crotch portion 98, and rear portion 100. Each portion 96, 98, 100 represents, in this embodiment, one-third of the length or structure of absorbent layer 86, as measured between absorbent back edge 88 and absorbent front edge 90 in a direction parallel to longitudinal centerline 110. Absorbent layer 86 desirably has a length between about 25 to about 70 centimeters, as measured in a direction parallel to centerline 110. Absorbent layer 86 also comprises absorbent front section 102 and absorbent back section 104. Absorbent section 102 extends from front edge 90 to inner absorbent wall 94, and includes front section surface 106. Back section 104 extends from inner absorbent wall 94 to back edge 88, and includes back section surface 108. Along with centerline 110, absorbent layer 86 has a transverse centerline 112. Longitudinal centerline 110 generally will coincide with longitudinal centerline 82 (FIG. 2) of article 20, while absorbent transverse centerline 112 may or may not coincide with transverse centerline 84 (FIG. 2) of article 20. Absorbent layer 86 also includes an absorbent bottom surface 146. Absorbent panel 92 desirably has a length between about 1 to about 10 centimeters, as measured in a direction parallel to centerline 110.

Although absorbent layer 86 and absorbent panel 92 have been described and illustrated, particularly in FIG. 12, as having clearly defined surfaces, edges, and sides, the present invention contemplates less clearly defined curved or sloping features. Consequently, the sides, edges, and surfaces may be curved or sloping, thus making it possibly difficult to discern precise or exact boundaries, such as the boundaries between inner absorbent wall 94, front section surface 106, and back section surface 108. In some cases, front section surface 106 and back section surface 108 can be generally flat, while inner absorbent wall 94 can provide a gently sloping transition in thickness between front section 102 and back section 104. In this case, inner absorbent wall 94 would comprise that gentle transition area or surface that extends between the generally flat front section surface 106 and generally flat back section surface 108. Regardless of the surface definitions, it is important to the present invention that the difference between front section thickness 116 and back section thickness 118 provides sufficient height or thickness for surge layer 114 (FIG. 3) to be positioned on back section 104 so that it is in substantially liquid communication with inner absorbent wall 94. Front section thickness 116 is measured between front section surface 106 and absorbent bottom surface 146, and back section thickness 118 is measured between back section surface 108 and absorbent bottom surface 146.

In other cases, both or only one of front section surface 106 and back section surface 108 can have a non-linear cross-sectional profile in the longitudinal or transverse dimension. As can be appreciated, multiple designs or constructions can be provided to absorbent layer 86 and absorbent panel 92. A specific design or construction will depend on, for example, the intended end-use of article 20, absorbent materials comprising absorbent structure 42, the dimensions of absorbent structure 42, or the like.

One suitable method of measuring the thickness of front section thickness 116 and back section thickness 118 is to employ Federal Test Method Standard (FTMS) No. 191 for nonwovens with the following modifications: (1) the diameter of the presser foot is 1.25 inches±0.001 inch, and (2) with an applied total load of 0.20 pounds per square inch±0.03 pounds per square inch to the specimen.

Absorbent layer 86 and absorbent panel 92 can comprise any suitable absorbent material, natural or synthetic, or a combination thereof; any suitable superabsorbent material or combination thereof; or any combination of absorbent material and superabsorbent material. Absorbent layer 86 and/or absorbent panel 92 may be wrapped in a tissue wrap (not shown) in order to maintain the integrity of the absorbent material. The superabsorbent materials may be organic or inorganic, and absorbent structure 42 can include from 0 to 100 weight percent of superabsorbent material. Suitable inorganic superabsorbent materials include, for example, absorbent clays and silica gels. Suitable organic superabsorbent materials can include natural materials, such as pectin, guar gum, and peat moss, as well as synthetic materials, such as synthetic hydrogel polymers. Such hydrogel polymers may include, for example, carboxymethylcellulose, alkali methyl salts of polyacrylic acids, polyacrylamides, polyvinyl alcohol, ethylene maleic anhydride copolymers, polyvinyl ethers, hydroxypropylcellulose, polymers and copolymers of vinyl sulfonic acid, polyacrylates, polyacrylamides, or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water insoluble. Cross-linking may, for example, be by irradiation or by covalent, ionic, van der Waals, or hydrogen bonding. Suitable materials are available from various commercial vendors, such as Dow Chemical Company, Hoechst-Celanese Corporation, and Allied Colloids, Inc. Typically, the superabsorbent material is capable of absorbing at least about 15 times its weight in water, and desirably is capable of absorbing more than about 25 times its weight in water. Absorbent layer 86 and absorbent panel 92 can also comprise cellulosic fibers, i.e., wood pulp fluff. One preferred type of wood pulp fluff is identified with the trade designation CR1654 from Kimberly-Clark Corporation, Neenah, Wis., and which is a bleached, highly absorbent sulphate wood pulp containing soft wood fibers.

In one embodiment, absorbent layer 86 is generally rectangular in shape, although other shapes can be used, and has a length between about 35 to about 38 centimeters and a width between about 7 to about 13 centimeters. The fluff and superabsorbent material in absorbent layer 86 are suitably present in a ratio of about 9 to about 20 grams fluff to about 7 to about 14 grams superabsorbent material, and absorbent layer 86 has a density within the range of about 0.10 grams per cubic centimeter to about 0.35 grams per cubic centimeter. A more detailed description of this particular absorbent can be found in U.S. patent application Ser. No. 08/096,654 filed Jul. 22, 1993, inventor Hanson et al., which is assigned to the assignee of this application, the content of which is incorporated by reference herein.

The superabsorbent material can be deposited in the fluff such that more superabsorbent material is concentrated adjacent to or near backsheet 44. The absorbent material, such as the fluff and SAM mixture described above, can also be zoned, in that a greater amount of absorbent material can be located in the center of absorbent layer 86 or toward the front or back of absorbent layer 86. It should also be understood that the fluff and superabsorbent material can be mixed in any desirable fashion or concentration, and that the superabsorbent material can exist as a discrete layer or layers within the fluff, or on top of, or below the fluff.

Absorbent layer 86 can also comprise, in one form, an air-laid nonwoven web comprising about 80 percent by weight fibrous superabsorbent material and about 20 percent by weight polymeric binder fibers. The fibrous superabsorbent material has a denier of about 9 d and a length of about 12 millimeters. Suitable fibrous superabsorbent materials are available from Technical Absorbents Ltd., United Kingdom, under the tradename OASIS. The polymeric binder fibers have a denier of about 3 d and a length of about 6 millimeters. Such binder fibers may be bicomponent fibers comprising about 50 percent by weight polyethylene and about 50 percent by weight polypropylene in a concentric sheath-core configuration. Suitable bicomponent binder fibers are available from Danaklon a/s of Varde, Denmark, under the tradename Danaklon AL Thermal-C. Such a composite web may be oven fused after air-laying for about five minutes at a temperature of about 150° Celsius. The composite web may have a basis weight of about 200 grams per square meter.

Absorbent panel 92 can have the same absorbent composition as absorbent layer 86, or can have an absorbent composition different from absorbent layer 86. In one embodiment, for example, absorbent layer 86 can be a mixture of fluff and superabsorbent material in a ratio of about 10 to about 12 grams of fluff to about 10 to about 12 grams of superabsorbent material, and can have a density from about 0.10 grams per cubic centimeter to about 0.35 grams per cubic centimeter. Absorbent panel 92 can be a layer of only superabsorbent material deposited on absorbent layer 86.

Absorbent panel 92 is shorter in length than absorbent layer 86, as measured along longitudinal centerline 110. The width and thickness of absorbent panel 92, relative to absorbent layer 86, can be the same or different. It is not necessary for absorbent panel 92 to have the same width or thickness as absorbent layer 86.

Referring now to FIG. 3, surge layer 114 is in substantially liquid communication with inner absorbent wall 94, absorbent panel 92, and absorbent layer 86. By "substantially liquid communication" is meant that a liquid can flow between, through, or along two or more mediums. Surge layer 114 may be placed on top of absorbent layer 86, as illustrated in FIG. 3, or may be placed on top of topsheet 40. Thus, the description of surge layer 114 as being "disposed", "disposed on" or "disposed with" absorbent layer 86, includes surge layer 114 being directly placed on or joined to absorbent layer 86, as illustrated in FIG. 3, or includes a third layer or element, such as topsheet 40, interposed between surge layer 114 and absorbent layer 86. Surge layer 114 is permeable to liquid, such as urine, when compressed under loads typically experienced during the wear of article 20.

Figure 14:
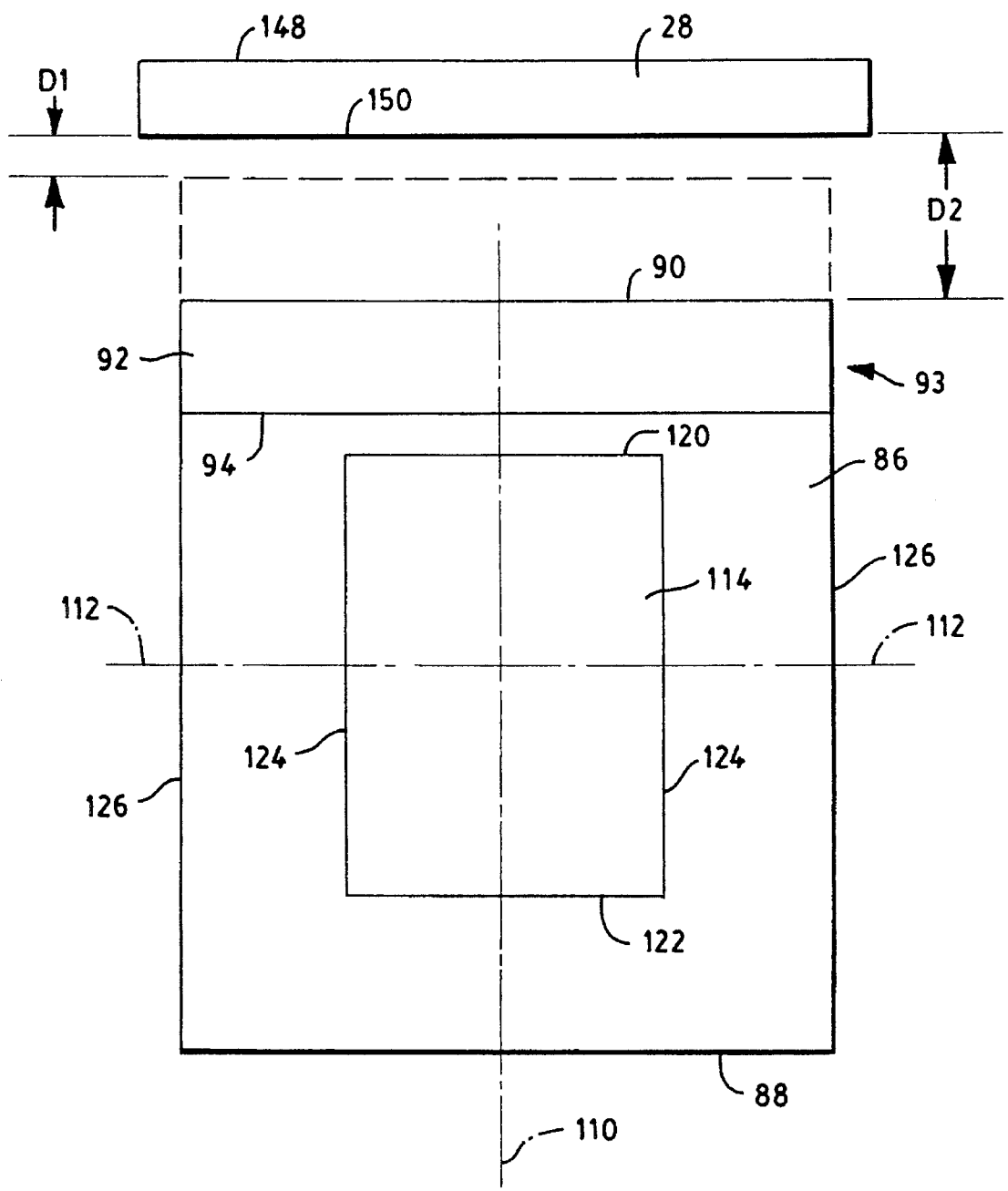
FIG. 14 illustrates a top plan view of the positional relationship between a waist elastic member and an absorbent.

The position, shape, and size of surge layer 114 may depend upon the material of which it is made, as well as the material of which topsheet 40 and absorbent layer 86 are made. Surge layer 114 may or may not extend the total width, i.e., transverse dimension, of absorbent layer 86, and generally will not extend the total length, as illustrated in FIG. 14. Surge layer 114 can be a through-air, bonded carded web; a spunbond bicomponent nonwoven web; a web of cross-linked cellulosic fibers; or the like. Surge layer 114 can have an overall basis weight of about 50 grams per square meter and an overall density of about 0.03 grams per cubic centimeter.

Surge layer 114 also can be a two-layer composite in which the first layer, which is the layer that will face toward the wearer's body, can have a basis weight of about 15 grams per square meter and comprise 100 percent polyethylene/polyester, sheath-core bicomponent fibers having a fiber denier of about 1.8 d to about 3 d. The second layer, which is the layer between the first layer and absorbent layer 86, can have a basis weight of about 35 grams per square meter and comprise a mixture of bicomponent fibers and single component fibers. The bicomponent fibers form about 40 percent by weight of the second layer. More particularly, about 35 percent by weight of the second layer is comprised of about 1.8 d polyethylene/polyester sheath-core fibers with a flat crimp, and about 5 percent by weight of the second layer is comprised of about 2 d polyethylene/polypropylene, sheath-core fibers with helical crimp. The single component fibers form about 60 percent by weight of the second layer, and are about 6 d polyester fibers configured with a flat crimp. The polyester fibers may or may not be hollow core fibers. Descriptions of other suitable materials of which surge layer 114 can be made are described in the aforementioned and incorporated U.S. patent application Ser. No. 08/096,654.

Referring to FIG. 14, absorbent layer 86 has respective opposite side edges 126, and surge layer 114 has respective opposite side edges 124 (FIG. 14). As illustrated in FIG. 14, each surge side edge 124 is spaced inwardly of a respective absorbent side edge 126, and surge back edge 122 is spaced inwardly of absorbent back edge 88. The term "spaced inwardly of" means that surge side edge 124 is nearer to absorbent longitudinal centerline 110 than absorbent side edge 126, and that surge back edge 122 is nearer to absorbent transverse centerline 112 than absorbent back edge 88.

Figure 13:
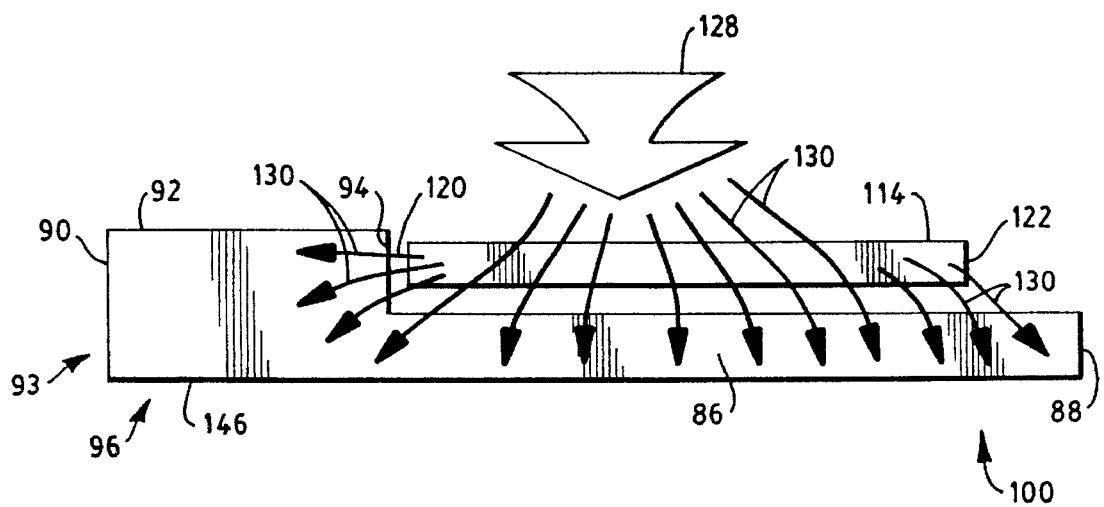
FIG. 13 illustrates a side elevational view of another absorbent and a surge layer showing the general flow characteristics of a liquid passing through the surge layer and into the absorbent.

Referring now to FIGS. 13 and 14, the front edge 120 of surge layer 114 is illustrated as being slightly spaced from inner absorbent wall 94. Although illustrated spaced from inner absorbent wall 94, front edge 120 of surge layer 114 may directly abut or contact inner absorbent wall 94, or may be spaced slightly therefrom a distance of about 5 millimeters or less. Any distance greater than about 5 millimeters will essentially prevent liquid communication between front edge 120 and wall 94. FIG. 13 illustrates in a generalized manner the purpose and function of surge layer 114 relative to absorbent layer 86 and absorbent panel 92. Surge layer 114 is capable of not only receiving liquid and having the liquid pass vertically therethrough, but also wicking or transporting the liquid in differently oriented directions relative to the plane of surge layer 114. Large arrow 128 illustrates a surge of liquid, such as urine, toward surge layer 114. Upon impacting surge layer 114, the liquid passes into and through surge layer 114, as illustrated by smaller arrows 130. Portions of the liquid are distributed within surge layer 114 so as to be deposited or transferred into various areas of absorbent layer 86. Looking at the right end of surge layer 114, as illustrated in FIG. 13, the last smaller arrow of liquid flow passes through back edge 122 and then into absorbent layer 86 in its rear portion 100. Similarly, the left side of surge layer 114, as illustrated in FIG. 13, has several smaller arrows 130 of liquid flow passing through surge front edge 120, through inner absorbent wall 94, and into absorbent panel 92. The greater number of smaller arrows 130 of liquid flow exiting front edge 120 of surge layer 114 illustrates the tendency, as explained earlier, of the liquid to move toward the front waist portion 22 (FIG. 1) of disposable article 20 when the wearer is in the prostrate position. Thus, one of the purposes of absorbent panel 92 is to provide additional absorbent capacity at the front portion 96 of absorbent layer 86.

Referring now to FIGS. 2, 3, and 4, a liquid impermeable baffle layer 132 is disposed between topsheet 40 and backsheet 44. Baffle layer 132, which can be made of the same liquid impermeable material as liquid impermeable backsheet 44, comprises front edge 134 and back edge 136, in which back edge 136 is illustrated as extending over inner absorbent wall 94 (FIG. 3) and front edge 120 of surge layer 114. Baffle layer 132 is suitably joined to topsheet 40 by, for example, adhesive 140, and to backsheet 44 by, for example, adhesive 142. Adhesive 142 only joins that portion of baffle layer 132 adjacent baffle front edge 134 to backsheet 44, as illustrated in FIG. 3. The remaining portion of baffle layer 132 is not joined to absorbent layer 86 or surge layer 114.

As illustrated in FIG. 4, the side portions 138 of baffle layer 132 are suitably joined, such as by adhesive 144, to backsheet 44. Adhesive 144 may join the full longitudinal length of side portions 138 to backsheet 44, or may join only a portion of the length of side portions 138 to backsheet 44.

As illustrated in FIG. 3, baffle layer 132 and that portion of topsheet 40 coincident therewith form an extensible configuration, such as the illustrated S-like design. The purpose for this is to provide extensibility to topsheet 40 and baffle layer 132 to accommodate the swelling of absorbent structure 42 as it absorbs liquid, such as urine. Absorbent panel 92 and front portion 96 (FIG. 12) of absorbent layer 86, will swell or extend in the vertical dimension, as viewed in FIG. 3. Absorbent layer 86 and absorbent panel 92 are considered "dry" prior to an insult, such as an urination, and are considered "wet" after an insult, such as an urination. Similarly, the thicknesses of absorbent layer 86 and absorbent panel 92 can be referred to as "dry" or "wet." The S-like design of baffle layer 132 and topsheet 40 provides sufficient excess material to allow baffle layer 132 and topsheet 40 also to extend or to move vertically under the force of the swelling of absorbent layer 86 and absorbent panel 92. The extensible design of baffle layer 132 and topsheet 40 is desired when baffle layer 132 and topsheet 40 are made of substantially inelastic materials. The difference, as it pertains to the present invention, between a material being "elastic" or "extensible" is that an extensible material will not necessarily tend to recover its original size and shape after removal of the force causing the deformation or extension, whereas an elastic material will tend to so recover.

The extensibility of baffle layer 132 and topsheet 40 should accommodate the swelling of absorbent layer 86 and absorbent panel 92, and will be dependent to a great degree upon the design of absorbent structure 42 and the absorbent material of which it is comprised. Generally, the front section thickness 116 (FIG. 12) has a dry thickness of about 7 millimeters or less, and a maximum wet thickness of about 13 millimeters or less. The maximum extension to be accommodated by baffle layer 132 and topsheet 40 is the difference between the maximum wet thickness and the dry thickness, which in this case is about 6 millimeters or less.

Referring primarily to FIGS. 3 and 14, front waist elastic member 28 comprises a front edge 148 and a back edge 150. One of the unique aspects of the present invention is the selected separation distance provided between back edge 150 and absorbent front edge 90. FIG. 14 illustrates in dashed lines one conventional placement or positioning of an absorbent layer or core. The distance D1 between waist elastic back edge 150 and the front edge of a conventionally positioned absorbent core is generally about 2 centimeters or less. In contrast, the selected separation distance D2 of the present invention between front waist elastic back edge 150 and front edge 90 is about 3 centimeters, desirably about 4 centimeters, and more desirably about 5 centimeters or more. This selected separation distance is important to the desired functioning and performance of waist elastic member 28. By providing this selected separation distance, absorbent front edge 90 and waist elastic back edge 150 are spaced farther apart than in most conventional articles of similar design. In the present invention, absorbent front edge 90 has been separated sufficiently from front waist elastic member 28 so that the absorbent material does not degrade or diminish the gasketing effect of waist elastic member 28 on article 20. As absorbent front edge 90 is positioned closer to waist elastic member 28, as with conventional positioning, it begins to enter or "invade" the area of elastic effect created by waist elastic member 28, thereby causing waist elastic member 28 to also gather absorbent front edge 90, thereby diminishing the gasketing effect of waist elastic member 28.

In use, the wearer, such as a child in the potty-training stage, will place his or her legs through waist opening 36 and a respective leg opening 38, and then pull article 20 upwardly to comfortably position article crotch portion 26, and place front waist portion 22 (FIG. 1) and back waist portion 24 at the waist of the wearer. Upon urination, particularly when the wearer is in the prostrate position, disposable absorbent article 20 provides improved containment of the urine at the wearer's waist. As illustrated in FIG. 13, surge layer 114 will receive and distribute the urine to absorbent panel 92 and absorbent layer 86. Since surge back edge 122 is spaced inwardly of absorbent back edge 88, urine passing through back edge 122 will be absorbed by absorbent back section 104 (FIG. 12). Urine moving in a forward direction, toward the left in FIG. 13, will be absorbed by front portion 96, which comprises absorbent panel 92 and absorbent front section 102 (FIG. 12). Baffle layer 132 (FIG. 3) provides a liquid barrier to urine moving in a direction toward backsheet front edge 48. As absorbent front portion 96 (FIG. 12) begins to swell or extend, baffle layer 132 and topsheet 40 will accommodate the swelling by also extending due to its extensible S-like design.

Figure 5:
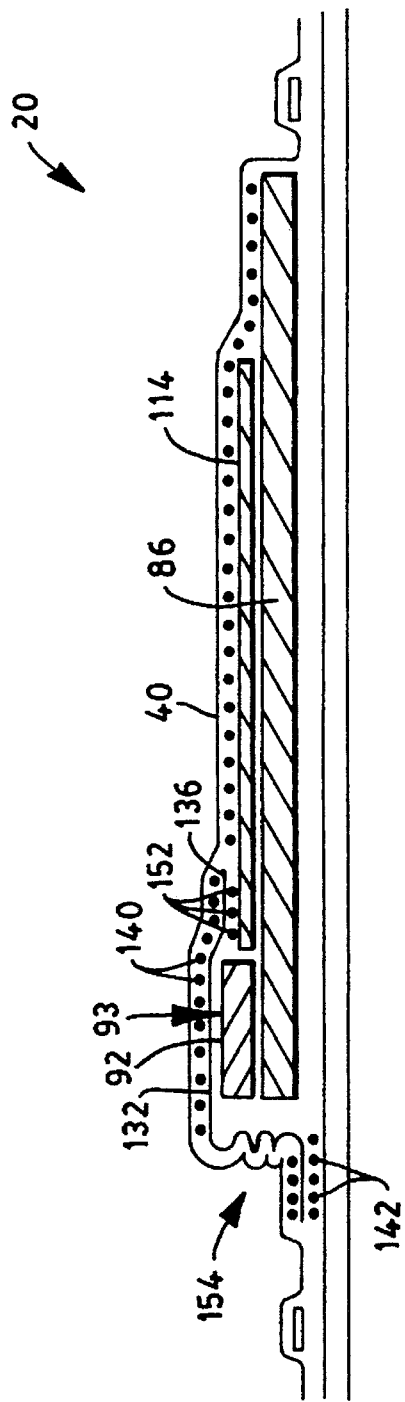
FIG. 5 illustrates a modification of the view of FIG. 3.

Various modifications of the above are contemplated by the present invention. For example, FIG. 5 illustrates absorbent panel 92 in the form of an absorbent element separate from absorbent layer 86. With regard to FIG. 5, elements or structure common to both FIG. 5 and FIG. 3 will keep the same reference numerals, and this will be the case with the remaining figures hereafter. Baffle layer 132 and topsheet 40 form an extensible gathered portion 154 to accommodate the extension or swelling of absorbent layer 86 and a separate absorbent panel 92. Extensible gathered portion 154 may or may not be pre-gathered prior to disposing baffle layer 132 and topsheet 40 with backsheet 44 and absorbent structure 42. One method of forming extensible gathered portion 154 is to overfeed, i.e., provide excess length of, topsheet 40 and baffle layer 132 relative to backsheet 44 during the manufacturing process.

As with baffle layer 132 in FIG. 3, baffle layer 132 is adhered to topsheet 40 by adhesive 140, and to backsheet 44 by adhesive 142. In addition, the back edge 136 of baffle layer 132 is suitably joined, such as by adhesive 152, to surge layer 114.

Figure 6:
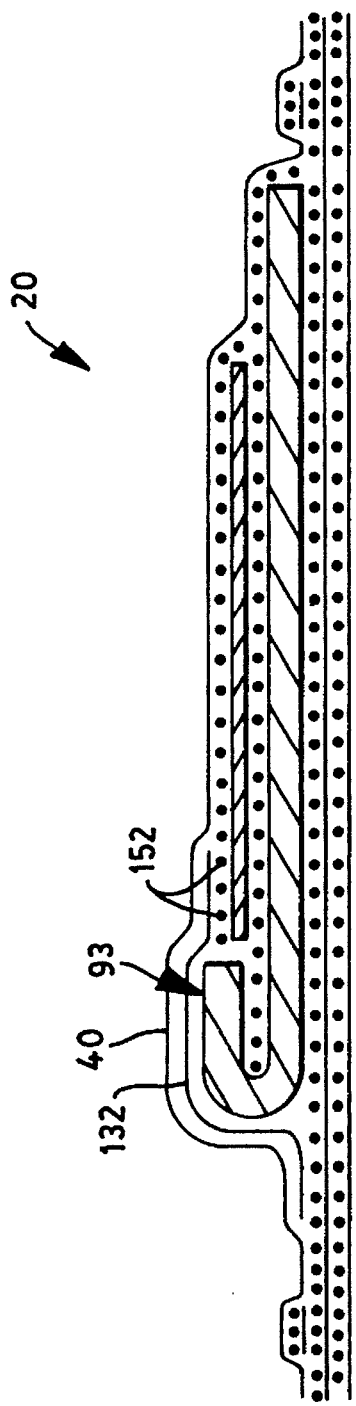
FIG. 6 illustrates a modification of the view of FIG. 3.

In the modification illustrated in FIG. 6, baffle layer 132 and at least that portion of topsheet 40 joined thereto are comprised of elastic materials. Thus, there is no gathered portion 154, since the elasticity of baffle layer 132 and topsheet 40 provide the desired extensibility. Suitable elastic materials are set forth in the aforementioned patents and patent applications incorporated by reference herein. Desirably, baffle layer 132 and the portion of topsheet 40 coincident therewith should have an elasticity between about 50 percent to about 200 percent. The term "elasticity" refers to that property of a material by virtue of which it tends to recover its original size and shape after removal of the force causing the deformation, and is expressed as a percent.

In FIG. 7, disposable absorbent article 20 is similar to that illustrated in FIG. 6 except that there is no adhesive 152 joining baffle layer 132 to surge layer 114.

FIG. 8 illustrates a modification in which a portion of surge layer 114 is sandwiched between absorbent panel 92 and absorbent layer 86. Baffle layer 132 includes a folded portion 156 suitably joined, such as by adhesive 158, to absorbent panel 92. Folded portion 156 desirably is positioned between absorbent panel 92 and surge layer 114.

FIG. 9 illustrates a modification in which absorbent front section 102 is formed by increasing the amount of absorbent material in absorbent layer 86 at front absorbent area 93. There is no separate or folded-over absorbent panel 92.

In another modification, absorbent panel 86 has more superabsorbent material zoned in front section 102 than is zoned in back section 104, and is uniform in thickness when dry. However, after an insult, the front section 102 will swell to a greater extent than back section 104 because of the increased amount of superabsorbent material zoned therein.

FIG. 10 illustrates a modification in which absorbent panel 92 is positioned between absorbent layer 86 and backsheet 44.

Figure 11:
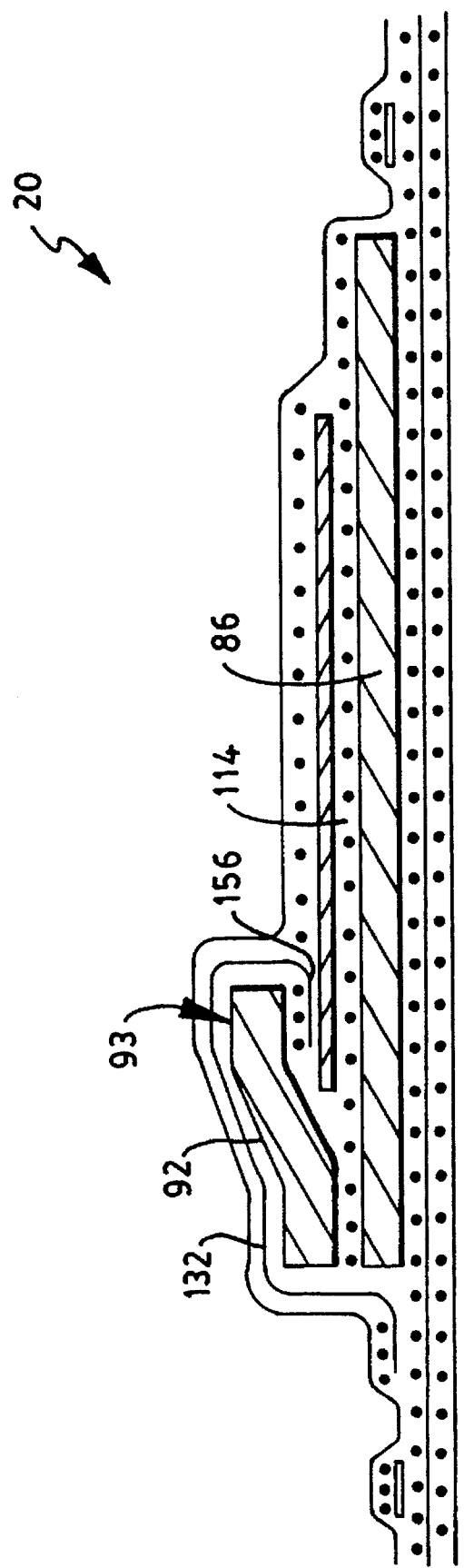
FIG. 11 illustrates a modification of the view of FIG. 3.

FIG. 11 illustrates a modification in which absorbent panel 92 and absorbent layer 86 sandwich a portion of surge layer 114, and baffle layer 132 comprises folded portion 156.

While this invention has been described as having a preferred embodiment, it will be understood that it is capable of further modifications. This application is therefore intended to cover any variations, equivalents, uses, or adaptations of the invention following the general principles thereof, and including such departures from the present disclosure as come or may come within known or customary practice in the art to which this invention pertains and fall within the limits of the appended claims.

What is claimed is:

1. A disposable absorbent article, comprising:

a backsheet comprising a front portion with a front edge and a back portion with a back edge, an absorbent structure disposed on said backsheet, said absorbent structure comprising (i) an absorbent layer comprising a front edge and a back edge, and a front section having a front section thickness and a front section surface, and a back section having a back section thickness and a back section surface, said front section thickness being greater than said back section thickness and defining an inner absorbent wall extending between said front section surface and said back section surface, (ii) a surge layer disposed on said absorbent layer, said surge layer comprising a front edge and a back edge, said surge layer front edge and said surge layer back edge being respectively spaced inwardly of said absorbent layer front edge and said absorbent layer back edge, said surge layer being in liquid communication with said inner absorbent wall, a liquid impermeable baffle layer overlying said front edge of said absorbent layer, and a waist elastic member joined at said backsheet front portion, said waist elastic member comprising a front edge and a back edge, said waist elastic member back edge being spaced from said front edge of said absorbent layer a distance of at least about 3 centimeters.

2. The article of claim 1 wherein said front edge of said surge layer is spaced from said inner absorbent wall a distance of about 5 millimeters or less.

3. The article of claim 2 wherein said front section thickness has a dry thickness of about 7 millimeters or less, and a maximum wet thickness of about 13 millimeters or less.

4. The article of claim 3 wherein said liquid impermeable baffle layer is extensible.

5. A disposable absorbent article, comprising:

a backsheet comprising a front portion with a front edge and a back portion with a back edge, and an absorbent structure disposed on said backsheet and comprising (i) a front section having a front section thickness and a front section surface, and a back section having a back section thickness and a back section surface, said front section thickness being greater than said back section thickness and defining an inner absorbent wall extending between said front section surface and said back section surface, and (ii) a surge layer disposed on said back section and being in substantial liquid communication with said inner absorbent wall, and having a front edge spaced from said inner absorbent wall a distance of about 5 millimeters or less, and a waist elastic member joined to said front portion of said backsheet, said waist elastic member having a back edge spaced from a front edge of said absorbent structure a distance of at least about 3 centimeters.

6. The article of claim 5 further comprising a liquid impermeable baffle layer overlying a front edge of said surge layer.

7. The article of claim 6 wherein said front section thickness has a dry thickness of about 7 millimeters or less, and a maximum wet thickness of about 13 millimeters or less.

8. The article of claim 6 wherein said baffle layer is extensible.

9. A disposable absorbent article, comprising:

a backsheet, an absorbent layer disposed on said backsheet, said absorbent layer comprising a front edge, a front portion, a crotch portion, and a rear portion, said front portion of said absorbent layer having an absorbent capacity greater than either said crotch portion or said rear portion, a liquid impermeable baffle layer overlying at least a portion of said front portion of said absorbent layer, and a waist elastic member joined to said backsheet, and comprising a front edge and a back edge, said back edge of said waist elastic member being spaced from said front edge of said absorbent layer a distance of at least about 3 centimeters.

10. The article of claim 9 further comprising a surge layer disposed on at least said crotch portion of said absorbent layer and being in substantially liquid communication with at least said front portion of said absorbent layer.

11. The article of claim 10 wherein said liquid impermeable baffle layer is extensible.

* * * * *